United States Patent [19]
Nordgren

[11] 3,956,048
[45] May 11, 1976

[54] METHOD FOR THE MANUFACTURING OF A DISPOSABLE OPERATION TEXTILE

[75] Inventor: Gunnar Nordgren, Paivarinta, Finland

[73] Assignee: Oy Suomen Vanutehdas-Finnwad Ltd., Helsinki, Finland

[22] Filed: Sept. 9, 1974

[21] Appl. No.: 504,209

[30] Foreign Application Priority Data
Sept. 11, 1973 Finland .............................. 2826/73

[52] U.S. Cl. .............................. 156/183; 128/132 D; 156/244
[51] Int. Cl.² .............................. A61F 13/00; B29F 3/00; B32B 31/12
[58] Field of Search ................ 156/62.2, 62.4, 62.8, 156/244, 245, 288, 183, 306, 309; 128/112, 113, 132 R, 132 D, 296, DIG. 18; 161/55, 69, 112, 152, 156, 227

[56] References Cited
UNITED STATES PATENTS

| | | | |
|---|---|---|---|
| 2,949,394 | 8/1960 | Rodman | 161/156 |
| 2,982,310 | 5/1961 | West | 156/62.2 |
| 3,423,277 | 1/1969 | Dipner | 128/132 D |
| 3,542,634 | 11/1970 | Such et al. | 128/132 D |
| 3,594,245 | 7/1971 | Hayes | 156/62.2 |
| 3,668,050 | 6/1972 | Donnelly | 128/132 D |
| 3,676,242 | 7/1972 | Prentice | 156/62.4 |
| 3,684,643 | 8/1972 | Stepp | 161/156 |
| 3,695,260 | 10/1972 | Endres | 128/132 D |
| 3,809,077 | 5/1974 | Hansen | 128/132 D |

*Primary Examiner*—Caleb Weston
*Attorney, Agent, or Firm*—Ladas, Parry, Von Gehr, Goldsmith & Deschamps

[57] ABSTRACT

A method for the manufacture of disposable operation textiles. In the method at least on first layer of a nonwoven fibre fabric material is fastened onto at least one second similar layer so that the principal fibre orientations of the layers become at least approximately perpendicular to each other. Said second layer is coated with a heat-sealable layer of synthetic material so that said layer in molten state and under tension is allowed to flow onto the web of fibre fabric. Then the combination is cooled whereby an internal prestress is produced and fixed in the coating of synthetic material. Said second layer is applied onto the first layer such that the layer of synthetic material comes against said first layer and the layers are fastened to each other by heat compression so that heat sealing occurs.

8 Claims, 1 Drawing Figure

U.S. Patent May 11, 1976 3,956,048
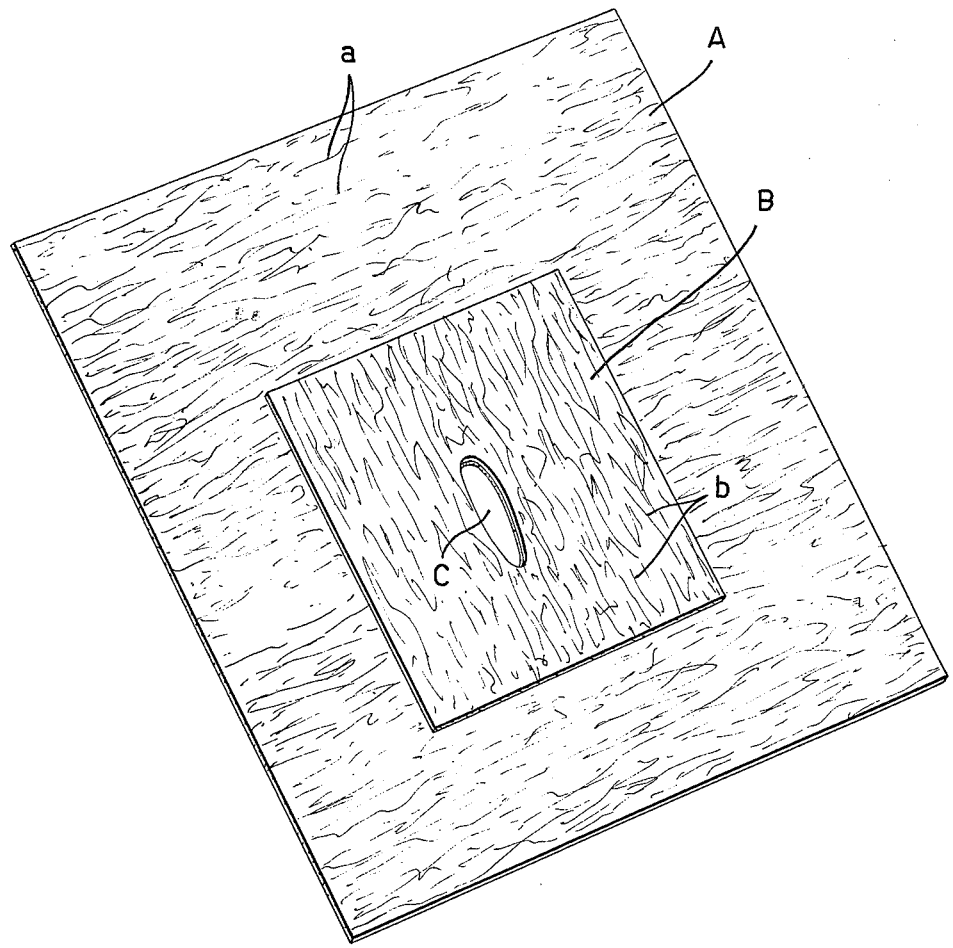

METHOD FOR THE MANUFACTURING OF A DISPOSABLE OPERATION TEXTILE

The present invention relates to a method for the manufacturing of disposable operation textiles out of such a non-woven fibre fabric material whose fibres are orientated in one direction more than in the direction perpendicular to said direction, wherein on at least one first layer is fastened at least one second layer so that the principal fibre orientations of the layers become at least approximately perpendicular to each other.

The purpose of such disposable operation textiles is, when placed at the point to be operated, in connection with the operation to protect the operating surgeon, on one hand, and the patient, on the other hand, from infections caused by bacteria. In this way it is possible to prevent what is called operation infection.

Since operation textiles which were used previously required washing, checking, patching, sterilization of the package, etc., this resulted in a high requirement of personnel. At the same time there was the risk of hospital infection in connection with keeping the contaminated laundry isolated.

This is why attempts have been made to develop disposable operation textiles which can be destroyed, e.g. by burning, without causing hospital infection. Among such disposable products should be mentioned, to begin with, sewn and glued disposable products. Sewn disposable products, however, involve several work steps at the sewing shop, which causes high production costs. Moreover, the maintaining of conditions of maximum hygiene during production becomes difficult.

Glueing is, on the other hand, untidy work and tends to pollute the environment, whereby the risk of bacteritic contamination increases in the production plant. The rate of progress of the work is low, and the glue also usually tends to harden the area of the seam or of the reinforcement to be glued.

Yarn-reinforced products of paper or of wood-fibre containing material have also been used. These are, however, usually of a more expensive rawmaterial, because the yarn must be produced and usually it must first be made into a net by glueing, which net is thereupon jointed between the paper layers by laminating. The paper layer may be coloured and water-repelling, but its short wood fibres cause a low wet-rubbing resistance, which results in the possibility of small, short-fibre fluff being produced. This fluff may, in connection with operations, cause growing together of stomach membranes and be harmful, for example, in eye operations.

Also, wood-fibre-containing disposable products without yarn reinforcement have been used. The drawbacks mentioned in the preceding paragraph (except the net) are also characteristic of these products.

Moreover, PVC-containing products have been used as disposable operation textile products. These have, however, involved the disadvantage that, when burnt in an incineration furnace, they release hydrogen chloride, which
   corrodes the flue construction of the furnace by transforming the plaster into $CaCl_2$,
   corrodes sheet roofs of buildings,
   is poisonous as gas.

Moreover, these products do not stand steam autoclave treatment.

In order to avoid the above drawbacks, a method has been developed in accordance with the present invention for the manufacturing of a disposable operation textile of several layers, and a novel product of highly practical characteristics is obtained. The invention is based on the observations set out below:

We have noticed that PE, which is used in an extrusion method for coating a fibrous fabric of rayon fibres whose fibres are orientated in the longitudinal direction more than in the transversal direction, owing to the method, stores in itself a prestress, which can be slackened when the product is heated afterwards, in which connection the fibrous fabric hereby shrinks in its longitudinal direction.

We have noticed that when a fibrous fabric coated in this way but of unslackened prestress is placed on another fibrous fabric of the same type so that the fibres are in the latter fabric substantially orientated in the transversal direction of the product, i.e. the fibres are in the two fabrics orientated so that their systems are substantially perpendicular to each other, and when the fabrics are pressed under heat and pressure by means of a press known from the textile industry, the above products are firmly heat-sealed together.

We have ascertained that if a fabric, rubber or any other base of a suitable pattern has been selected for the presing base in the cloth press, this pattern is partly transferred to the heat-sealed final product.

We have ascertained that a laminate produced in this way by heat-sealing stands steam sterilization, although a general opinion is that PE does not stand steam sterilization.

We have ascertained that during such a steam sterilization the prestress of PE mentioned above is slackened and by its shrinkage produces wrinkles in the fibrous fabric.

We have ascertained that the said pattern produced is emphasized after heat sterilization through the slackening of the stress in the PE layer and through the subsequent shrinkage, whereby more regular patterns and wrinkles can be produced.

On the basis of the above, the method in accordance with the invention is mainly characterized in that
   the material of the second layer is prepared by, in a way known per se, coating a web of fibrous fabric by the extrusion method with a heat-sealable layer of synthetic material so that the layer of synthetic material is, as molten and under tension, allowed to flow onto the web of fibrous fabric, whereupon the combination in this way produced is cooled, whereby an internal prestress is produced and fixed in the coating of synthetic material,
   the second layer coated in this way is applied onto the first layer at a desired location so that the layer of synthetic material comes against the first layer,
   the layers are fastened to each other by heat-compression, whereby the layers are heat-sealed to each other.
   means embodiments of the method in accordance with the invention are, on the other hand, defined in patent claims 2 to 13. By meas of the invention, among other things, the following advantages are achieved:
   Fast and simple production.
   Tidy production.
   When burnt in an incineration furnace, the product does not develop poisonous gases.
   When burnt in an incineration furnace, the product does not develop corrosive gases.

When burnt in an incineration furnace, the product does not develop gases spoiling the flue of the furnace.

The wrinkle or pattern produced in the product refracts the rays of light and is agreeable to the eye.

The wrinkle or pattern produced in the product prevents slipping of instruments.

The wrinkle produced in the product softens the reinforcement in the operation textile.

The arrangement of the fibres substantially as perpendicular to each other increases the tear strength of the product, in particular so when using of sheet pliers is concerned, whereby tensile stress follows after punching of the product.

The product being suitable for steam sterilization also involves good economy, because steam sterilization is the cheapest and the most reliable method of sterilization.

Below, the invention will be examined more closely with the aid of the embodiment in accordance with the attached drawing. The drawing shows an operation cloth that consists of a base or trunk piece A and a reinforcement piece B placed on same. As comes out from the drawing, the principal fibre orientation in piece A, illustrated by the broken lines $a$, is substantially perpendicular to the corresponding fibre orientation $b$ in the reinforcement piece B. An operation opening C has been punched in the operation cloth within the area limited by the reinforcement piece B.

The trunk piece A is a green, for example, 40 g/sq.m fibrous fabric of, for example, 50 mm 1.7 dtex rayon fibre and bound by a vinylacetate-acrylate copolymer, made water- and blood repellent by means of wax-metal salts, but penetrable to air.

The dimensions of the trunk piece may be, for example, 70 × 80 cm.

The reinforcement piece B is a green, for example, 40 g/sq.m fibrous fabric of, for example, 50 mm 1.7 dtex rayon fibre and bound, for example, by a vinylacetate-acrylate copolymer, absorbing water and blood, and by means of the meltextrusion method coated with 15 g/sq.m polyethylene.

The dimensions of the reinforcement part may be, for example, 35 × 48 cm.

In the production of the product it is possible to use a what is called glue cloth press whose dimensions are, for example, 1400 × 400 mm. The compression force is preferably approximately 0.7 kg/sq.cm, the compression temperature approximately 165°C, and the duration of compression about 7 seconds. In order to produce a pattern, a what is called sack cloth is used, whose warp density is 2.3 per cm ad weft density likewise 2.3 per cm and the yarn number tex 300.

The products to be produced can be operation sheets, hole cloths, branch cloths, and equivalent.

Thus, the manufacturing takes place so that the reinforcement piece B, with the polyethylene layer downwards, is placed onto the trunk piece A at the desired point, whereupon the compression, is accomplished by the above glue cloth press, whereby the trunk piece A and the reinforcement piece B are heat-sealed together so that the polyethylene layer remains in between the fibrous-cloth layers.

It is preferable, even though not necessary, to use a pattern base on the compression discs of the press, which base produces wrinkles especially within the area of the reinforcement piece B. Such a pattern base can be used either on both press halves of the press or only on one of them, whereby, in the latter case, the pattern base is preferably placed on the half next to the reinforcement piece B.

It should be mentioned that the coating of the production piece with polyethylene takes place in a way known per se by the melt-extrusion method so that the polyethylene web flowing as molten in the vertical direction is tensioned before it is placed onto the web of fibrous fabric, whereupon this combination is cooled, whereby a certain prestress is stored therein. The manufacturing can take place, for example, so that the polyethylene flows down as a molten film from the nozzle in between a cold roller and the web of fibrous fabric, whereby the polyethylene melts into the fibrous fabric. When the coating is cooled so as to form, together with the base, a structure that has the common properties of the coating and the base, the prestress is produced and fixed in the coating.

Thus, it should be noticed that after compression the product has only a certain intial wrinkledness which is shrunk together only when the product is being sterilized in the steam autoclave, in this way producing the final wrinkledness.

The sterilization is carried out by means of saturated vapour whose temperature is 143°C and pressure 3 kg/sq.cm (above atmospheric pressure), and it takes 6 to 15 minutes, during which period the stress in the PE layer slackens and the PE layer tends to shrink, whereby the desired final patterning and wrinkledness are achieved.

It is evident that the method in accordance with the present invention is applicable to the manufacturing of other kinds of operation textiles as well, for example to the manufacturing of textiles of more than two layers, such as 3, 4, 5 or 6 layers, by using the same principle. It is also possible to use other heat-sealable synthetic materials except polyethylene, for example polypropylene. The products obtained in this way are, however, not quite equally good, because they become somewhat brittle in connection with steam sterilization. Also, it is possible to use as a heat-sealable synthetic material some polymer, copolymer or single- or multilayer films thereof.

In stead of the sack cloth, it is possible to use, for example, a what is called waffle-iron base in order to produce a more distinct pattern.

The operation opening C can be made either in advance or in connection with the operation by punching, cutting or in any other way without a sewn seam.

What I claim is:

1. A method of manufacturing disposable textile sheets for surgical operations, which comprises the combination of the following steps:

a. coating a side of a web of non-woven rayon fiber fabric, having the fibers thereof principally oriented in one direction, by extruding thereon a molten heat-sealable layer of synthetic material under tension selected from polyethylene and polypropylene;

b. cooling said coated web to produce and fix in said layer an internal prestress;

c. superimposing the coated side of said cooled coated web onto another web of non-woven rayon fiber fabric having the fibers thereof principally oriented in a direction substantially perpendicular to the orientation direction of the fibers of the coated web; and d. applying heat and compression to said superimposed webs whereby said webs are heat sealed together.

2. A method as claimed in claim 1, characterized in that the heat-compression is carried out by means of a glue-cloth press.

3. A method as claimed in claim 1, characterized in that the compression force is 0.5 to 1.0 Kg/sq.cm, compression temperature 150° to 180°C, and duration of the compression 4 to 10 seconds.

4. A method as claimed in claim 1, characterized in that a patterned compression base is used in order to produce an initial patterning or initial wrinkledness at least on said cooled coated web of said textile sheet.

5. A method as claimed in claim 4, characterized in that the compression base is a patterned rubber base.

6. A method as claimed in claim 4, characterized in that the compression base has waffle-iron patterning.

7. A method as claimed in claim 4, characterized in that the compression base is a sack cloth.

8. A method as claimed in claim 7, characterized in that the warp density of the sack cloth is 2.3 per cm, the weft density 2.3 per cm, and the yarn number tex 300.

* * * * *